(12) United States Patent
Otake et al.

(10) Patent No.: US 11,439,146 B2
(45) Date of Patent: Sep. 13, 2022

(54) ANTI-ACANTHAMOEBA CONTACT LENS SOLUTION

(71) Applicant: SEED CO., LTD., Tokyo (JP)

(72) Inventors: Hideyuki Otake, Tokyo (JP); Yoshinori Yanagawa, Tokyo (JP); Hiroyuki Nawase, Tokyo (JP)

(73) Assignee: SEED CO., LTD., Tokyo (JP)

( * ) Notice: Subject to any disclaimer, the term of this patent is extended or adjusted under 35 U.S.C. 154(b) by 254 days.

(21) Appl. No.: 16/077,936

(22) PCT Filed: Feb. 16, 2017

(86) PCT No.: PCT/JP2017/005636
§ 371 (c)(1),
(2) Date: Aug. 14, 2018

(87) PCT Pub. No.: WO2017/142005
PCT Pub. Date: Aug. 24, 2017

(65) Prior Publication Data
US 2019/0327968 A1    Oct. 31, 2019

(30) Foreign Application Priority Data
Feb. 17, 2016 (JP) .............................. JP2016-027865

(51) Int. Cl.
*A01N 43/36* (2006.01)
*A01N 25/04* (2006.01)
*A61L 12/14* (2006.01)

(52) U.S. Cl.
CPC ............. *A01N 43/36* (2013.01); *A01N 25/04* (2013.01); *A61L 12/145* (2013.01)

(58) Field of Classification Search
None
See application file for complete search history.

(56) References Cited

U.S. PATENT DOCUMENTS

| 4,443,429 | A | | 4/1984 | Smith et al. | |
|---|---|---|---|---|---|
| 5,380,303 | A | * | 1/1995 | Holly | A01N 33/12 424/427 |
| 5,382,599 | A | | 1/1995 | Rupp et al. | |
| 2006/0122080 | A1 | | 6/2006 | Mori | |
| 2006/0205621 | A1 | | 9/2006 | Borazjani et al. | |

FOREIGN PATENT DOCUMENTS

| EP | 0 923 950 | A2 | | 6/1999 | |
|---|---|---|---|---|---|
| EP | 0923950 | A2 | * | 6/1999 | ........... A61L 12/145 |
| EP | 2 932 985 | A1 | | 10/2015 | |
| JP | 09-506518 | A | | 6/1997 | |
| JP | 11-249087 | A | | 9/1999 | |
| JP | 2002-143277 | A | | 5/2002 | |
| JP | 2006-509532 | A | | 3/2006 | |
| JP | 3894945 | B2 | | 3/2007 | |
| JP | 2011-246458 | A | | 12/2011 | |
| JP | 2013097022 | A | * | 5/2013 | |
| JP | 2013-234176 | A | | 11/2013 | |
| JP | 2014-218461 | A | | 11/2014 | |
| KR | 10-2010-0061403 | A | | 6/2010 | |
| WO | WO 2013/154209 | A1 | | 10/2013 | |

OTHER PUBLICATIONS

Cometics & toiletries (https://www.cosmeticsandtoiletries.com/formulating/function/moisturizer/premium-Profile-of-Polyquaternium-6-210999891.html), no pagination. (Year: 2013).*
Marquart et al. (J. of Opthamology, 2013, 9 pages. (Year: 2013).*
Lens101.com discussion board, no pagination "https://www.lens101.com/contact-lens-care-questions/138605-opti-free-solution-eye-drop.html" Entries dated May 29, 2012-May 30, 2012. (Year: 2012).*
Lubrizol Bath&Shower/Conditioning polymers differentiation chart (file:///C:/Users/ehirt/Downloads/Bath%20and%20Shower%20Conditioning%20Agents.pdf), no pagination, no date.*
Written Opinion dated Nov. 18, 2019, in Singapore Patent Application No. 11201806918Q.
Office Action dated Mar. 13, 2020, in Chinese Patent Application No. 201780011787.3.
Extended European Search Report dated Jun. 11, 2019, in European Patent Application No. 17753260.3.
International Search Report for PCT/JP2017/005636 (PCT/ISA/210) dated Apr. 11, 2017.
Notification of Reasons for Refusal for Japanese Patent Application No. 2018-500186, dated Jun. 4, 2018.
Notification of Reasons for Refusal for Japanese Patent Application No. 2018-500186, dated Mar. 27, 2018.
Written Opinion of the International Searching Authority for PCT/JP2017/005636 (PCT/ISA/237) dated Apr. 11, 2017.
English translation of International Preliminary Report on Patentability and Written Opinion dated Aug. 30, 2018, in PCT/JP2017/005636 (Forms PCT/IB/326, PCT/IB/373, and PCT/ISA/237).
European Office Action dated Sep. 3, 2020 for Application No. 17 753 260.3.
Vietnamese Office Action for Vietnamese Application No. 1-2018-03589, dated Feb. 28, 2022, with an English translation.

* cited by examiner

*Primary Examiner* — Erin E Hirt
(74) *Attorney, Agent, or Firm* — Birch, Stewart, Kolasch & Birch, LLP

(57) ABSTRACT

The objective of the present invention is to provide a contact lens solution that is safer to eyes such that it has little or no effects on eye tissue and has the versatility that makes the solution applicable to a wide range of contact lenses, while exhibiting desirable anti-*Acanthamoeba* activity. The objective is achieved by the anti-*Acanthamoeba* contact lens solution containing a cationic polymer having an average molecular weight in a range of 150,000 to 1,600,000 and having in its molecule a diallyldimethylammonium chloride unit and an inorganic salt.

11 Claims, No Drawings

ANTI-ACANTHAMOEBA CONTACT LENS SOLUTION

CROSS-REFERENCE TO RELATED APPLICATION

The present application claims the benefit of priority to Japanese Patent Application No. 2016-27865 filed on Feb. 17, 2016, the disclosure of which is incorporated herein by reference in its entirety.

TECHNICAL FIELD

The present invention relates to a contact lens solution used to care for contact lenses and for other purposes.

BACKGROUND ART

When contact lenses are worn on eyes, protein and lipid contaminants from tears and rheum often adhere to the contact lens surfaces. If the contact lenses with these contaminants are continuously worn on eyes, not only will the wear comfort and vision correction performance of the contact lenses deteriorate, but wearers will also be subjected to the risk of eye diseases because microorganisms propagate on the contact lens.

One of such eye diseases is *Acanthamoeba keratitis* caused by the infection of cornea with microbes of genus *Acanthamoeba*. *Acanthamoeba keratitis* causes intense pain in the eye and may result in corneal perforation and loss of vision in severe cases. The number of reported cases of the disease has increased recently.

In many cases, wearing contact lenses contaminated with *Acanthamoeba* causes *Acanthamoeba keratitis*. For example, contact lenses may be contaminated with *Acanthamoeba* present in tap water when they are washed with tap water for storage. Wearing these contact lenses contaminated with *Acanthamoeba* causes *Acanthamoeba keratitis*.

Typically, *Acanthamoeba keratitis* treatment is carried out with scraping off the cornea and administration of antifungal agents. However, *Acanthamoeba keratitis* is an refractory infectious disease because it is difficult to be diagnosed at an early stage, and the burden to patients is heavier because recurrence of inflammation is likely, leading to prolonged treatment, and the cornea may be scarred during the treatment. Thus, various attempts have been made thus far to develop medicinal agents that can prevent contamination with *Acanthamoeba*.

For example, Patent Document 1 listed below, the disclosure of which is incorporated herein by reference in its entirety, discloses an anti-*Acanthamoeba* disinfectant/preservative for use with contact lenses containing an effective amount of polylysine. Patent Document 2 listed below, the disclosure of which is incorporated herein by reference in its entirety, discloses an anti-*Acanthamoeba* composition that contains, as an active ingredient, a glycoprotein lactoferrin or lactoferricin that is a peptide product of enzymatic degradation of lactoferrin. Patent Document 3 listed below, the disclosure of which is incorporated herein by reference in its entirety, discloses an anti-protozoan composition containing a Candin-family drug Caspofungin and a biguanide compound as active ingredients.

In recent years, various multi-purpose solutions (MPSs) are commercially available that can serve to wash, rinse, disinfect and preserve contact lenses in one solution. These MPSs are easy to handle and are now widely used. Organic nitrogen disinfectants are common disinfecting components added to MPSs. For example, Patent Document 4 listed below, the disclosure of which is incorporated herein by reference in its entirety, discloses a preventive and therapeutic drug for *Acanthamoeba keratitis* that is applicable to MPS, containing two components, an organic nitrogen disinfectant and a diallyldialkyl ammonium-containing polymer (MW=1,000 to 150,000), as active ingredients.

PRIOR ART DOCUMENT

Patent Document

Patent Document 1: JP 2002-143277 A
Patent Document 2: JP 2011-246458 A
Patent Document 3: JP 2013-234176 A
Patent Document 4: JP 2014-218461 A

DISCLOSURE OF INVENTION

Problems to be Solved by the Invention

Nonetheless, the drugs and compositions described in Patent Documents 1 to 4 each have associated drawbacks. Because of the polylysine active ingredient, use of the anti-*Acanthamoeba* disinfectant/preservative described in Patent Document 1 is limited to particular types of contact lenses: it cannot be applied to high-water, ionic hydrated soft contact lenses (group IV). Thus, the disinfectant/preservative lacks versatility.

The glycoprotein or the peptide product of degradation of the glycoprotein used as the active ingredients in the anti-*Acanthamoeba* composition described in Patent Document 2 leads to deposition of the protein and peptide on the eye tissue, which may cause impaired vision or eye disorder.

Caspofungin, which is the active ingredient used in the anti-protozoan composition described in Patent Document 3 and which exhibits anti-fungal activity by inhibiting the activity of 1,3-beta-glucan synthase that is the major component of fungal cell walls, may cause various side effects, including anaphylaxis, liver dysfunction and eye pruritus.

The preventive and therapeutic drug for *Acanthamoeba keratitis* described in Patent Document 4 has similar problems to the anti-protozoan composition described in Patent Document 3. Specifically, the preventive and therapeutic drug for *Acanthamoeba keratitis* described in Patent Document 4, which contains the organic nitrogen disinfectant as one of its active ingredients, may cause various side effects, including anaphylaxis, liver dysfunction and eye pruritus, depending on the type and amount of the organic nitrogen disinfectant.

As described, despite their microbicidal activity against *Acanthamoeba* (i.e., anti-*Acanthamoeba* activity) that results from their respective active ingredients, each of the drugs and compositions described in Patent Documents 1 to 4 has its own drawbacks with respect to the safety to eye tissue and versatility to make them applicable to a wide range of contact lenses.

It is an objective of the present invention to provide a contact lens solution which has not only desirable anti-*Acanthamoeba* effect but is safer such that it has little or no effects on ocular tissue while it is versatile and applicable to a wide range of contact lenses.

Means of Solving the Problems

The disinfecting components to be added to contact lens solutions, such as MPS, may have either low molecular weights or high molecular weights. When an MPS containing a low-molecular-weight disinfecting component is used to wash and disinfect contact lenses, the low-molecular-weight disinfecting component tends to adhere to the surface of contact lenses or tends to be incorporated into the contact lenses. The low-molecular-weight disinfecting agent adhered to or incorporated into the contact lenses may come into contact with the eye tissue of the wearer who wears the contact lenses and may subject the wearer to the risk of eye disorder.

On the other hand, when high-molecular-weight disinfecting components are employed, they tend to have reduced disinfecting effects although they are safe on the eye tissue. Therefore, a contact lens solution containing a high-molecular-weight disinfecting component may not exhibit sufficient disinfecting effects against *Acanthamoeba*, which is more difficult to kill than common bacteria and fungi.

In order to solve the objective, taking into consideration the above-described common technical knowledge in the art, the present inventors have conducted extensive studies to develop components that have little or no adverse effects on eye tissue while exhibiting disinfecting effects against *Acanthamoeba*. As a consequence, the present inventors have found that certain cationic polymers with a predetermined structure and an average molecular weight within a predetermined range, when used with an inorganic salt, exhibit an excellent disinfecting effect against *Acanthamoeba*. Based on this finding, the present inventors have succeeded in creating an anti-*Acanthamoeba* contact lens solution containing the cationic polymer and the inorganic salt. Such an anti-*Acanthamoeba* contact lens solution is safe on eye tissue and has versatility that makes it applicable to various contact lenses, while exhibiting an anti-*Acanthamoeba* effect. It is these findings and successful examples that have led to the completion of the present invention.

Accordingly, one aspect of the present invention provides an anti-*Acanthamoeba* contact lens solution containing a cationic polymer having an average molecular weight in a range of 150,000 to 1,600,000 and having in its molecule a diallyldimethylammonium chloride unit represented by the following general formula (I):

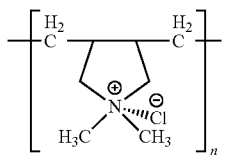

(I)

wherein n is an integer determined such that the average molecular weight of the polymer is in the range specified above); and an inorganic salt.

In one embodiment of the anti-*Acanthamoeba* contact lens solution of the present invention, the cationic polymer is preferably a cationic polymer having an average molecular weight in a range of 150,000 to 1,200,000 and having in its molecule the diallyldimethylammonium chloride unit as the only polymer unit or a cationic polymer having an average molecular weight in a range of 150,000 to 1,200,000 and having in its molecule the diallyldimethylammonium chloride unit and an acrylamide unit and/or an acrylic acid unit as polymer units.

In one embodiment of the anti-*Acanthamoeba* contact lens solution of the present invention, the cationic polymer is preferably a cationic polymer having an average molecular weight in a range of 200,000 to 500,000.

In one embodiment of the anti-*Acanthamoeba* contact lens solution of the present invention, the cationic polymer is preferably polyquaternium-6 or polyquaternium-7.

In one embodiment of the anti-*Acanthamoeba* contact lens solution of the present invention, the inorganic salt is preferably an inorganic salt selected from the group consisting of sodium salt, potassium salt, calcium salt and magnesium salt.

In one embodiment of the anti-*Acanthamoeba* contact lens solution of the present invention, the anti-*Acanthamoeba* contact lens solution is preferably an anti-*Acanthamoeba* contact lens solution free of any organic nitrogen disinfectant.

In one embodiment of the anti-*Acanthamoeba* contact lens solution of the present invention, the anti-*Acanthamoeba* contact lens solution preferably further contains a chelating agent selected from the group consisting of edetic acid, sodium edetate, disodium edetate, ethylenediaminetetraacetic acid, nitrilotriacetic acid, trihydroxymethylaminomethane, citric acid and tartaric acid.

Advantageous Effects of the Invention

The anti-*Acanthamoeba* contact lens solution in one embodiment of the present invention uses a cationic polymer having a specific structure and an average molecular weight within a specific range such that the solution is highly safe for use on eye tissue regardless of the presence or absence of organic nitrogen disinfectants commonly added to contact lens care solutions such as MPS and has versatility that makes the solution applicable to a wide range of contact lenses while exhibiting excellent disinfecting effect against *Acanthamoeba*.

The anti-*Acanthamoeba* contact lens solution in one embodiment of the present invention can be used to wash and store contact lenses in order to reduce or avoid the risk that the wearer of the contact lenses is affected with keratitis caused by *Acanthamoeba*.

MODES FOR CARRYING OUT THE INVENTION

While the anti-*Acanthamoeba* contact lens solution in accordance with one aspect of the present invention will now be described in further details, the scope of the present invention is not limited to what is described in this section; rather, the present invention may take various other forms to the extent that its objectives are achieved.

The anti-*Acanthamoeba* contact lens solution is characterized in that it contains a cationic polymer having a specific structure and a specific average molecular weight, and an inorganic salt. The anti-*Acanthamoeba* contact lens solution has an activity to kill, or inhibit the propagation of, at least one type of *Acanthamoeba* (i.e., Anti-*Acanthamoeba* activity). As used herein, the terms disinfection or sterilization may refer to killing, removal or inhibition of propagation of microorganisms.

The degree of anti-*Acanthamoeba* effect of the anti-*Acanthamoeba* contact lens solution is not particularly limited as long as it can be confirmed that the anti-*Acanthamoeba* contact lens solution kills, or inhibits the propagation of, at least one type of *Acanthamoeba*. For example, the degree of the anti-*Acanthamoeba* effect is such that the dead cell rate of the ATCC 50514 strain of *Acanthamoeba castellanii* as determined by the evaluation method 1 for the effects of disinfecting *Acanthamoeba* as described later in Examples is 20% or higher, preferably 40% or higher, more preferably 60% or higher, and even more preferably 80% or higher, or such that the logarithmic difference after *Acanthamoeba* disinfection time as determined by the evaluation method 2 for the effects of disinfecting *Acanthamoeba* as described later in Examples is 0.8 or higher, preferably 0.9 or higher, more preferably 1.0 or higher, and even more preferably 2.0 or higher.

While the degree of safety of the anti-*Acanthamoeba* contact lens solution is not particularly limited as long as the solution does not bring about significant changes in the eye tissue of the wearer of the contact lens, such as itchiness and deterioration of vision, it is such that, for example, the relative colony formation rate with the concentration adjusted to 2.5 v/v % is 75% or higher, preferably, the relative colony formation rate with the concentration adjusted to 5 v/v % is 75% or higher, or more preferably, the relative colony formation rate with the concentration adjusted to 10 v/v % is 75% or higher when the safety is evaluated by the method described later in Examples.

While the degree of the shape stability of the anti-*Acanthamoeba* contact lens solution is not particularly limited as long as the solution does not bring about significant changes in the shape of applied contact lenses, it is such that, for example, the amount of change in diameter is within ±1.0 mm, preferably within ±0.5 mm, and more preferably within ±0.2 mm when the shape stability is evaluated by the method described later in Examples.

A preferred embodiment of the cationic polymer is a cationic polymer having an average molecular weight within a range of 150,000 to 1,600,000 and structurally at least having in its molecule a diallyldimethylammonium chloride unit represented by the following general formula (I):

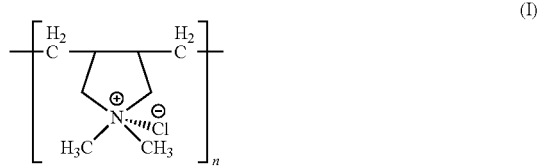

(I)

wherein n is an integer determined such that the average molecular weight of the polymer is in the range specified above.

For example, the average molecular weight of the cationic polymer is preferably from 150,000 to 1,200,000, more preferably from 180,000 to 1,200,000, and still more preferably from 200,000 to 500,000 in order for the anti-*Acanthamoeba* contact lens solution to exhibit the anti-*Acanthamoeba* effects and to provide the safety on eye tissue.

Specific examples of preferred embodiments of the cationic polymer include cationic polymers having in their molecules the diallyldimethylammonium chloride unit represented by the general formula (I) as the only polymer unit; cationic polymers having in their molecules the diallyldimethylammonium chloride unit represented by the general formula (I) and an acrylamide unit as polymer units; cationic polymers having in their molecules the diallyldimethylammonium chloride unit represented by the general formula (I) and an acrylic acid unit as polymer units; and cationic polymers having in their molecules the diallyldimethylammonium chloride unit represented by the general formula (I), an acrylamide unit and an acrylic acid unit as polymer units.

Each polymer unit of the cationic polymer may be either substituted or unsubstituted. The structure of the terminals of the cationic polymer is not particularly limited. However, the sum of the degree of polymerization of the respective polymer units of the cationic polymer is determined so that the resulting polymer has the above-described molecular weight.

Specific examples of the cationic polymer include, but are not limited to, polyquaternium-6, polyquaternium-7, polyquaternium-22 and polyquaternium-39 each having a molecular weight within the above-specified range. Preferred specific examples of the cationic polymer are polyquaternium-6 and polyquaternium-7 with polyquaternium-6 more preferred. The above-described cationic polymers may be used in the anti-*Acanthamoeba* contact lens solution either individually or in combination of two or more.

The cationic polymer may be obtained by any non-limited method: for example, when the cationic polymer is polyquaternium-6, it can be obtained by using a water-soluble monomer of diallyldimethylammonium chloride as a starting material and subjecting it to cyclic polymerization by a radial polymerization initiator such as peroxides or by light to forma linear homopolymer.

The cationic polymer may be a commercially available product. For example, polyquaternium-6, which is represented by the general formula $(C_8H_{16}N.Cl)$ x (wherein x is an integer representing the degree of polymerization), is commercially available as the following products: MERQUAT 100 (MW: 150,000) from Lubrizol, ME POLYMER H-40 W (MW: 240,000) from TOHO Chemical Industry, COSMUAT VG (MW: 200,000) from SENKA Corporation, UNISENCE FPA 1001 L (MW: 200,000) from SENKA Corporation, UNISENCE FPA 1002 L (MW: 500,000) from SENKA Corporation, UNISENCE FPA 7000 E (MW: 1,200,000) from SENKA Corporation, and PAS-H-10 L (MW: 200,000) from NITTOBO MEDICAL (each polymer name denotes registered trademark or product name). Polyquaternium-6 may be a polychlorodimethylmethylene piperidinium solution described in Japanese Standards of Quasi-drug Ingredients 2006 (GAIGENKI).

For example, polyquaternium-7, which is represented by the general formula $(C_8H_{16}N.Cl)x-(C_3H_5NO)$ (wherein x is an integer representing the degree of polymerization), is commercially available as the following products: MERQUAT 2200 (MW: 1,600,000) from Lubrizol, MERQUAT 740 (MW: 120,000) from Lubrizol, MERQUAT CG 600 (MW: 1,200,000) from Lubrizol, ME POLYMER 09 W (MW: 450,000) from TORO Chemical Industry, COSMUAT VHK (MW: 1,600,000) from SENKA Corporation, COSMUAT VH (MW: 1,600,000) from SENKA Corporation, COSMUAT VHL (MW: 200,000) from SENKA Corporation, and PAS-J-81 (MW: 180,000) from NITTOBO MEDICAL (each polymer name denotes registered trademark or product name). Polyquaternium-7 may be dimethyldiallylammonium chloride/acrylamide copolymer solution described in Japanese Standards of Quasi-drug Ingredients (GAIGENKI).

The amount of the cationic polymer contained is not particularly limited as long as the anti-*Acanthamoeba* contact lens solution exhibits anti-*Acanthamoeba* effects. For example, if taking into consideration that the cationic polymer has an effect on the disinfecting effects, the amount of the cationic polymer is preferably from $1.0 \times 10^{-5}$ to 10.0 w/v %, more preferably from $5.0 \times 10^{-5}$ to 1.0 w/v %, still more preferably from $1.0 \times 10^{-4}$ to 0.01 w/v %, and still even more preferably from $5.0 \times 10^{-4}$ to 0.005 w/v %. If the amount of the cationic polymer is less than $1.0 \times 10^{-5}$ w/v %, then the resulting disinfecting effects will be effective against bacteria and fungi, but may not be sufficiently effective against *Acanthamoeba*.

The anti-*Acanthamoeba* contact lens solution contains an inorganic salt along with the cationic polymer. The type of the inorganic salt is not particularly limited: examples include inorganic alkali metal salts and inorganic alkaline earth metal salts. Preferred examples include inorganic sodium salts, inorganic potassium salts, inorganic calcium salts and inorganic magnesium salts. More preferred examples include sodium chloride, potassium chloride, calcium chloride, magnesium carbonate, magnesium chloride and magnesium sulfate. The inorganic salts may be used either individually or in combination or two or more.

While the amount of the inorganic salt is not particularly limited, the amount is for example from 0.01 to 10 w/v %, preferably from 0.1 to 5 w/v %, more preferably from 0.5 to 2 w/v %, and still more preferably from 0.5 to 1.5 w/v %. The amount of the inorganic salt can be suitably determined by taking into consideration the irritation to eye tissue and osmotic pressure caused when the anti-*Acanthamoeba* contact lens solution is applied to the wearer of the contact lens.

While the ratio of the cationic polymer to the inorganic salt (cationic polymer: inorganic salt) is not particularly limited as long as the anti-*Acanthamoeba* contact lens solution exhibits the anti-*Acanthamoeba* effects, the ratio of the cationic polymer to the inorganic salt is for example from 1:1 to 100,000, preferably from 1:10 to 50,000, more preferably from 1:10 to 10,000, still more preferably from 1:20 to 10,000, and still even more preferably from 1:50 to 10,000. In order for the anti-*Acanthamoeba* contact lens solution to provide enhanced anti-*Acanthamoeba* effects, the amount of the cationic polymer is from $5.0 \times 10^{-5}$ to 0.1 w/v %, preferably $1.0 \times 10^{-4}$ to 0.05 w/v %, and more preferably from $2.5 \times 10^{-4}$ to 0.01 w/v % and the ratio of the cationic polymer to the inorganic salt (cationic polymer: inorganic salt) is preferably from 1:50 to 10,000.

In addition to the cationic polymer and the inorganic salt, the anti-*Acanthamoeba* contact lens solution may further contain other additives that may typically be added to contact lens care solutions as long as such additives do not interfere with the objectives of the invention. The other additives are not particularly limited: examples include disinfectants, surfactants, buffers, chelating agents, thickeners, humectants, isotonic agents, and enzymes such as proteases and lipases. It should be noted, however, that since some disinfectants may affect eye tissue or may be allergens, anti-*Acanthamoeba* contact lens solutions, due to the conditions such as the eye tissue and allergic diathesis of the wearer of the contact lens, are generally divided into two categories: those containing a cationic polymer and an inorganic salt and further containing a disinfectant, and those containing a cationic polymer and an inorganic salt, but no disinfectants.

The disinfectant is not particularly limited: examples include biguanide-based disinfectants, such as polyhexamethylene biguanide (PHMB), polyaminopropyl biguanide, alexidine and chlorhexidine gluconate (GCH); quaternary ammonium-based disinfectants, such as benzalkonium chloride, benzethonium chloride and polidronium chloride; iodine-based disinfectants, such as povidone iodine; and hydrogen peroxide disinfectants. Preferred examples include organic nitrogen-based disinfectants. More preferred examples include PHMB.

The disinfectant may be a commercially available product or may be produced by any known method. While the amount of the disinfectant is not particularly limited, the amount may be reduced from what is typically used in contact lens care solutions since the cationic polymer and the inorganic salt present in the anti-*Acanthamoeba* contact lens solution serve to provide the anti-*Acanthamoeba* effects. Specifically, the amount of the disinfectant is preferably 2.0 w/v % or less in view of the safety issue such as eye irritation.

Preferably, the anti-*Acanthamoeba* contact lens solution may further contain surfactants to remove fats and other contaminants adhering to the contact lenses. While the surfactant is not particularly limited, those that do not affect contact lenses and is confirmed to be safe on eyes are preferably selected from anionic surfactants, cationic surfactants, nonionic surfactants and amphoteric surfactants. Nonionic surfactants are particularly preferred because of their high cleaning performance.

Specific examples of nonionic surfactants include polyoxyethylene-polyoxypropylene block polymers, polyoxyethylene alkyl ethers, polyoxyethylene alkylphenyl ethers, polyoxyethylene hydrogenated castor oil, polyoxyalkyl esters, and polyoxyethylene sorbitan alkyl esters. Of these, polyoxyethylene-polyoxypropylene block copolymers are preferred.

Specific examples of the polyoxyethylene-polyoxypropylene block polymer are commercially available as the following products: ADEKA Pluronic F-88 from ADEKA (polyoxyethyene [200] polyoxypropylene [40] glycol), Pluronic F68 from BASF (polyoxyethyene [160] polyoxypropylene [30] glycol), and Pluronic F127 from BASF (polyoxyethylene [196] polyoxypropylene [67] glycol) (each polymer name denotes registered trademark or product name). The amount of the surfactant is not particularly limited: for example, the amount of the surfactant is from about 0.01 to about 5.0 w/v %, and preferably from 0.03 to 1.0 w/v %, which is typical in contact lens care agents.

The pH, osmotic pressure and other physical properties of the anti-*Acanthamoeba* contact lens solution are not particularly limited as long as these properties allow the solution to exhibit the anti-*Acanthamoeba* effects. Preferably, the anti-*Acanthamoeba* contact lens solution has a pH in the range of 6.4 to 8.4 and more preferably in the range of 6.8 to 7.8 in view of irritation to eye. A buffer is preferably added to adjust the pH to these ranges.

The buffer is not particularly limited and may be any buffer commonly used as a contact lens care agent, including, for example, phosphate buffers, borate buffers, citrate buffers, glycine buffers, and tris(trishydroxyaminomethane) buffers. Borate buffers are preferably used in the anti-*Acanthamoeba* contact lens solution in view of disinfecting effects of *Acanthamoeba* (See, for example, JP H6-321715 A; Journal of Japan Contact Lens Society, vol. 50, No. 4, pp. 234-237, each of which is incorporated herein by reference in its entirety) and because borate buffers can enhance the anti-*Acanthamoeba* effects as compared to phosphate buffers and citrate buffers. When present in too small an amount, the buffer may not provide the desired buffering effects whereas too much buffer may cause irritation to eye and may precipitate at low temperatures. Thus, the amount of buffer is for example from 0.01 to 5.0 w/v % and preferably from 0.05 to 1.0 w/v %.

The chelating agent is not particularly limited and may be any chelating agent commonly used as a contact lens care agent, including, for example, polycarboxylic acids such as edetic acid, sodium edetate, disodium edetate, ethylenediaminetetraacetic acid, nitrilotriacetic acid, trihydroxymethylaminomethane, citric acid and tartaric acid, and salts thereof. The amount of the chelating agent is not particularly limited and may be any amount commonly used as a contact lens care agent: for example, the amount of the chelating agent is from 0.001 to 2.0 w/v %, and preferably from 0.01 to 1.0 w/v %.

The thickener is not particularly limited and may be any thickener commonly used as a contact lens care agent, including, for example, hydroxyethyl cellulose, hydroxypropyl methylcellulose, carboxy cellulose sodium salt, and polyvinyl alcohol.

The isotonic agent is not particularly limited and may be any isotonic agent commonly used as a contact lens care agent, including, for example, glycerin, propylene glycol, propanediol, mannitol, sorbitol and sucrose.

The humectant is not particularly limited and may be any humectant commonly used as a contact lens care agent, including, for example, hyaluronic acid, collagen, amino acids and salts thereof, pyrrolidone carboxylic acid salts, polyvinyl alcohol, and MPC polymers such as 2-methacryloyloxyethyl phosphorylcholine polymers and 2-methacryloyloxyethyl phosphorylcholine/butyl methacrylate copolymers and derivatives thereof.

The resulting anti-*Acanthamoeba* contact lens solution obtained by adding the above-described additives preferably has a final osmotic pressure in a physiological range of 200 to 400 mmol/kg, and more preferably in the range of 220 to 380 mmol/kg.

The anti-*Acanthamoeba* contact lens solution may be produced according to any of the production methods known in the art of ophthalmology in a non-limited manner. For example, it can be prepared by adding the cationic polymer and the inorganic salt and optionally the buffer, surfactant and other additives to purified water either simultaneously or sequentially. The anti-*Acanthamoeba* contact lens solution in the form of a liquid composition may then be filled in a container made of a material commonly used for containing a contact lens care agent, which may optionally be subjected to sterilization by heat or other treatments for use by consumers.

The anti-*Acanthamoeba* contact lens solution may be, not particularly limited, used in any suitable manner that exhibits anti-*Acanthamoeba* effects for contact lenses: for example, it may be used in the form of an eye drop directly applied to the eyes of the contact lens wearer; it may be indirectly applied to the eye tissue or infected site of the contact lens wearer; or it may be used in the form of a solution for washing and storing the contact lenses to disinfect the contact lenses. One preferred form of the anti-*Acanthamoeba* contact lens solution is an anti-*Acanthamoeba* contact lens care agent for washing and/or storing contact lenses, preferably soft contact lenses.

The present invention will now be described more specifically with reference to the following Examples, which are not intended to limit the present invention. The present invention may take various forms to the extent that the objectives of the present invention are achieved.

Examples

[Preparation of Test Samples]

Test samples of Examples 1 to 18 and Comparative Examples 1 to 15 were prepared according to the formulations shown in Tables 1 and 2 (the unit of the amounts of components in the tables is w/v %). Specifically, the components shown in Tables 1 and 2 (the amounts of polyquaternium 6 and polyquaternium 7 were for pure components) were weighed and added to 100 mL of purified water, and the mixtures were thoroughly stirred at room temperature until uniform. The resulting uniform solutions were sterilized by filtering through a cellulose acetate filter with the pore size of 0.2 μm to form anti-*Acanthamoeba* contact lens solutions as test samples. PLURONIC POLOXAMER 407 (BASF) was used as the nonionic surfactant. MPS (1) and MPS (2), which are contact lens solutions, are Commercial Product 1 (active ingredient PQ-1:0.001 w/v %) and Commercial Product 2 (active ingredient PHMB: 0.00011 w/v %), respectively.

[Evaluation Method 1 for Disinfection Effects against *Acanthamoeba*]

*Acanthamoeba castellanii* ATCC 50514 was used as the test strain.

*Acanthamoeba* cultured on a liquid medium (ATCC 712 medium) at 25° C. was collected and centrifuged. Ringer 1/4 solution was then added to suspend the *Acanthamoeba* to a concentration of $10^7$ to $10^8$ (cfu/ml) to form an *Acanthamoeba* test solution.

0.1 mL of the *Acanthamoeba* test solution was inoculated into 10 mL of each test sample of Examples 1 to 5 and Comparative Examples 1 to 4 and the resulting mixtures were allowed to undergo a disinfection process by incubating at 25° C. for four hours. This resulted in evaluation solutions.

After the incubation period, 0.4 w/v % Trypan Blue solution was added to each evaluation solution and the total cell number, viable cell number and dead cell number were counted using a hemocytometer by optical microscope. Based on the counts, the dead cell rate was calculated as the percentage of dead cells relative to the total number of cells. The solutions were rated based on the dead cell rates according to the following criteria. The results are shown in Table 1.

A circle (○) indicates that the dead cell rate was 60% or higher.

A triangle (Δ) indicates that the dead cell rate was 20% or higher and below 60%.

A cross (x) indicates that the dead cell rate was below 20%.

[Evaluation Method 2 for Disinfection Effects against *Acanthamoeba*]

*Acanthamoeba castellanii* ATCC 50514 was used as the test strain.

*Acanthamoeba* cultured on a liquid medium (ATCC 712 medium) at 25° C. was collected and centrifuged. Ringer 1/4 solution was then added to suspend the *Acanthamoeba* to a concentration of $10^7$ to $10^8$ (cfu/ml) to form an *Acanthamoeba* test solution.

0.1 mL of the *Acanthamoeba* test solution was inoculated into 10 mL of each test sample of Examples 6 to 18, Comparative Examples 5 to 15, and MPS (1) and (2), and the resulting mixtures were allowed to undergo a disinfection process by incubating at 25° C. for four hours. This resulted in evaluation solutions.

After the incubation period, 1 mL of each evaluation solution was taken and 9 mL of an inactivating agent (10% polysorbate 1/4 Ringer solution) was added. The solution was then serially diluted with an liquid medium (ATCC 712 medium) to form 4.6-fold serial dilutions. The evaluation solutions of five different concentration points near 10 to $10^4$ (cfu/ml) were prepared with proper dilution factors.

0.2 mL of each evaluation solution at each concentration point was poured into three wells of a 48-well culture plate. The culture plate with the poured evaluation solution was incubated for seven days, and the difference in logarithm in the number of *Acanthamoeba* before and after disinfect treatment (i.e., decrease in the number of viable cells) was subsequently determined for each evaluation solution according to the quantification method (MTT method) described in the Reference Literature given below (the description of which is incorporated herein by reference in its entirety).

Evaluation solutions for which a 1.0 or greater logarithmic difference was observed were determined to be test samples with disinfecting effects. In comparing the disinfecting ability between test samples, evaluation solutions for which a 0.5 or higher decrease in the number of viable cells was observed were determined to be test samples with significant disinfecting effects. The results of evaluation are shown in Table 2.

Reference Literature: The MTT Assay: A Quantitative Method to Evaluate the Inactivation of *Acanthamoeba*: J. Antibact. Antifung. Agents Vol. 42, No. 10, pp 527-532 (2014)

[Evaluation Method for Disinfection Effects Against Bacteria]

*Pseudomonas aeruginosa* is known to cause corneal infection, which is the most common disease attributable to contact lenses among contact lens wearers. Hence, *Pseudomonas aeruginosa* ATCC 9027 was used as the test strain in testing the disinfection effects.

*P. aeruginosa* was cultured on a slant agar medium at 35° C. for 18 hours. Subsequently, Dulbecco's phosphate buffered saline was added to suspend the *P. aeruginosa* to form a stock bacteria solution. The stock bacteria solution was further diluted with Dulbecco's phosphate buffered saline to adjust the concentration to $10^5$ to $10^6$ cfu/mL to form test bacteria solutions. Soybean casein agar medium was used as the agar medium.

0.1 mL of the test bacteria solution was inoculated into 10 mL of each test sample of Examples 6 to 18, Comparative Examples 5 to 15, and MPS (1) and (2), and the resulting mixtures were allowed to undergo a disinfection process by incubating at 25° C. for four hours. This resulted in evaluation solutions. After the incubation period, 1 mL of each evaluation solution was added to 9 mL of a medium containing an inactivating agent (Neutralizing broth) (10-fold dilution). This solution was further serially diluted with Dulbecco's phosphate buffered saline to make 10-fold serial dilutions. 1 ml each of the evaluation solutions of three different concentration points with proper dilution factors was poured into a dispodish. Agar medium was then added and the mixture was incubated at 35° C. for 48 hours. The resulting colonies were counted to determine the number of viable cells.

The initial cell number, which is the bacterial cell number in the test bacterial solution, was determined by forming 10-fold serial dilutions with Dulbecco's phosphate buffered saline and using the agar medium plate method as described above.

The difference in logarithm in the cell number (i.e., decrease in the number of viable cells) after the disinfection process was determined for each test sample from the initial cell number and the number of viable cells in each evaluation solution inoculated with the test bacteria solution (in logarithmic values) using the following equation:

[Decrease in the number of viable cells]=Initial cell number−The number of viable cells in the evaluation solution The decrease in the number of viable cells determined by the equation above (logarithmic difference) serves as a measure of disinfection effects. The test samples are typically rated for the disinfection effects according to the primary criteria of the ISO stand-alone test. Specifically, test samples for which the decrease in the number of viable cells of bacteria during the four-hour disinfection period was 3.0 or higher were determined to have disinfecting effects. Also, in comparing the disinfecting ability between test samples, test samples for which the difference in the number of viable cells was 0.5 or higher were determined to be test samples with significant disinfecting effects.

[Safety]

V79 Chinese hamster lung cells precultured in a $CO_2$ incubator at 37° C. were treated with trypsin and then suspended in an Eagle's minimum essential medium containing fetal bovine serum to prepare a cell suspension.

Test samples of Examples, Comparative Examples, and MPS (1) and MPS (2) shown in Table 3 were added to the wells of a culture plate at the sample concentrations (v/v %) of 20%, 10%, 5% and 2.5%. The cell suspension was then added so that each well contained 100 cells. The cells were cultured in a $CO_2$ incubator at 37° C. for seven days. As a control, cells were cultured on the medium under the same conditions.

The relative colony formation rate was determined for each sample at each concentration point using the following equation:

[Relative colony formation rate] (%)=(The number of colonies at each concentration point/The number of colonies in Control)×100

The relative colony formation rate (%) was directly used as a measure of the safety on eye tissue and the relative colony formation rates (%) at the same concentration were compared to evaluate the safety of respective samples according to the following criteria. The results of evaluation are shown in Table 3.

A circle (○) indicates that the relative colony formation rate (%) was 75% or higher.

A triangle (Δ) indicates that the relative colony formation rate (%) was 50% or higher and below 75%.

A cross (x) indicates that the relative colony formation rate (%) was below 50%.

[Shape Stability of Contact Lens]

SEED 2-week Fine UV (group I) and SEED 2-week Pure (group IV) (both from SEED) were used as test lenses.

The contact lenses were removed from the blister packs and the surface moisture was removed. Each lens was then placed in a lens case, into which 3.5 mL of each of Examples 1 to 4, Comparative Examples 1 to 3, and commercial products MPS (1) and MPS (2) was added and the lenses were left for two weeks. Subsequently, the diameter of the contact lenses was measured using a microscope. A lens was evaluated as "passed" for the shape stability when the change in diameter before and after the lens was washed by rubbing 30 times according to the contact lens approval standard was within ±0.2 mm relative to the value indicated for the product. The results of the evaluation are shown in Table 1.

TABLE 1

| Components | Examples | | | | | Comparative Examples | | | |
|---|---|---|---|---|---|---|---|---|---|
| | 1 | 2 | 3 | 4 | 5 | 1 | 2 | 3 | 4 |
| Boric acid | 0.15 | 0.15 | 0.15 | 0.15 | 0.15 | 0.15 | 0.15 | 0.15 | 0.15 |
| Borax | 0.05 | 0.05 | 0.05 | 0.05 | 0.05 | 0.05 | 0.05 | 0.05 | 0.05 |
| Sodium chloride | 0.65 | 0.65 | 0.65 | 0.65 | 0.65 | 0.65 | 0.65 | 0.65 | 0.65 |
| Potassium chloride | 0.15 | 0.15 | 0.15 | 0.15 | 0.15 | 0.15 | 0.15 | 0.15 | 0.15 |
| EDTA•2Na | 0.05 | 0.05 | 0.05 | 0.05 | 0.05 | 0.05 | 0.05 | 0.05 | 0.05 |
| PHMB | — | — | — | — | — | — | 0.0001 | — | — |
| PQ-6 (M.W. 8500) | — | — | — | — | — | — | — | 0.01 | — |
| PQ-6 (M.W. 150000) | 0.01 | — | — | — | — | — | — | — | — |
| PQ-6 (M.W. 240000) | — | 0.01 | — | — | — | — | — | — | — |
| PQ-6 (M.W. 500000) | — | — | 0.01 | — | — | — | — | — | — |
| PQ-6 (M.W. 1200000) | — | — | — | 0.01 | — | — | — | — | — |
| PQ-7 (M.W. 10000) | — | — | — | — | — | — | — | — | 0.01 |
| PQ-7 (M.W. 180000) | — | — | — | — | 0.01 | — | — | — | — |
| Shape Stability | ○ | ○ | ○ | ○ | | Δ | Δ | Δ | |
| *Acanthamoeba castellanii* | ○ | ○ | ○ | ○ | ○ | X | X | X | X |

TABLE 2

| Components | Examples | | | | | | | | | |
|---|---|---|---|---|---|---|---|---|---|---|
| | 6 | 7 | 8 | 9 | 10 | 11 | 12 | 13 | 14 | 15 |
| Boric acid | 0.15 | 0.15 | 0.15 | 0.15 | 0.15 | 0.15 | 0.15 | 0.15 | 0.15 | 0.15 |
| Borax | 0.05 | 0.05 | 0.05 | 0.05 | 0.05 | 0.05 | 0.05 | 0.05 | 0.05 | 0.05 |
| Sodium chloride | 0.65 | 0.65 | 0.65 | 0.65 | 0.65 | 0.65 | 0.65 | 0.65 | 0.65 | 0.65 |
| Potassium chloride | 0.15 | 0.15 | 0.15 | 0.15 | 0.15 | 0.5 | 0.15 | 0.15 | 0.15 | 0.15 |
| EDTA•2Na | 0.05 | 0.05 | 0.05 | 0.05 | 0.05 | 0.05 | 0.05 | 0.05 | 0.05 | 0.05 |
| Nonionic surfactants | — | — | — | — | — | — | — | — | — | — |
| PHMB | — | — | — | — | — | — | — | — | — | — |
| PQ-6 (M.W. 8500) | — | — | — | — | — | — | — | — | — | — |
| PQ-6 (M.W. 150000) | — | — | — | — | 0.001 | — | — | — | 0.002 | 0.0005 |
| PQ-6 (M.W. 240000) | 0.002 | 0.001 | 0.0005 | 0.0001 | — | — | — | — | — | — |
| PQ-6 (M.W. 500000) | — | — | — | — | — | — | 0.001 | — | — | — |
| PQ-6 (M.W. 1200000) | — | — | — | — | — | — | — | 0.001 | — | — |
| PQ-7 (M.W. 10000) | — | — | — | — | — | — | — | — | — | — |
| PQ-7 (M.W. 180000) | — | — | — | — | — | — | — | 0.001 | — | — |
| pH | 7.6 | 7.6 | 7.6 | 7.6 | 7.6 | 7.6 | 7.6 | 7.6 | 7.6 | 7.6 |
| Osmotic pressure (mOms) | 274 | 274 | 274 | 274 | 274 | 274 | 274 | 274 | 274 | 274 |
| Osmotic pressure rate (osmatic pressure 286) | 0.96 | 0.96 | 0.96 | 0.96 | 0.96 | 0.96 | 0.96 | 0.96 | 0.96 | 0.96 |
| *Acanthamoeba castellanii* | 3.34 | 3.03 | 2.01 | 1.15 | 2.60 | 3.28 | 3.33 | 2.73 | 3.30 | 2.08 |
| *Pseudomonas aeruginosa* | >5.00 | >5.00 | 4.78 | 4.65 | 4.88 | >5.00 | >5.00 | 4.68 | >5.00 | 4.68 |

| Components | Examples | | | Comparative Examples | | | | | | |
|---|---|---|---|---|---|---|---|---|---|---|
| | 16 | 17 | 18 | 5 | 6 | 7 | 8 | 9 | 10 | 11 |
| Boric acid | 0.15 | 0.15 | 0.15 | 0.15 | 0.15 | 0.15 | 0.15 | 0.15 | 0.15 | 0.5 |
| Borax | 0.05 | 0.05 | 0.05 | 0.05 | 0.05 | 0.05 | 0.05 | 0.05 | 0.05 | 0.05 |
| Sodium chloride | 0.65 | — | 0.75 | 0.65 | 0.65 | 0.65 | 0.65 | 0.65 | 0.65 | 0.65 |
| Potassium chloride | 0.15 | 1.00 | — | 0.15 | 0.15 | 0.15 | 0.15 | 0.15 | 0.15 | 0.15 |
| EDTA•2Na | 0.05 | 0.05 | 0.05 | 0.05 | 0.05 | 0.05 | 0.05 | 0.05 | 0.05 | 0.05 |
| Nonionic surfactants | — | — | — | — | — | — | — | 0.05 | — | — |
| PHMB | — | — | — | — | 0.0001 | 0.0002 | — | — | 0.0001 | — |
| PQ-6 (M.W. 8500) | — | — | — | — | — | — | 0.001 | 0.001 | 0.001 | — |
| PQ-6 (M.W. 150000) | 0.0001 | — | — | — | — | — | — | — | — | — |
| PQ-6 (M.W. 240000) | — | 0.001 | 0.001 | — | — | — | — | — | — | — |
| PQ-6 (M.W. 500000) | — | — | — | — | — | — | — | — | — | — |
| PQ-6 (M.W. 1200000) | — | — | — | — | — | — | — | — | — | — |
| PQ-7 (M.W. 10000) | — | — | — | — | — | — | — | — | — | 0.001 |
| PQ-7 (M.W. 180000) | — | — | — | — | — | — | — | — | — | — |
| pH | 7.6 | 7.8 | 7.8 | 7.6 | 7.6 | 7.6 | 7.6 | 7.6 | 7.6 | 7.6 |
| Osmotic pressure (mOms) | 274 | 279 | 274 | 274 | 274 | 274 | 274 | 274 | 274 | 274 |
| Osmotic pressure rate (osmatic pressure 286) | 0.96 | 0.98 | 0.97 | 0.96 | 0.96 | 0.96 | 0.96 | 0.96 | 0.96 | 0.96 |

TABLE 2-continued

| | | | | | | | | | |
|---|---|---|---|---|---|---|---|---|---|
| Acanthamoeba castellanii | 1.00 | 2.25 | 2.30 | 0.14 | 0.45 | 0.62 | 0.65 | 0.70 | 0.79 | 0.74 |
| Pseudomonas aeruginosa | 4.65 | >5.00 | >5.00 | 0.36 | 4.71 | >5.25 | 4.82 | 5.00 | >5.25 | 4.68 |

| | Comparative Examples | | | | | |
|---|---|---|---|---|---|---|
| Components | 12 | 13 | 14 | 15 | MPS(1) | MPS(2) |
| Boric acid | 0.15 | — | — | — | | |
| Borax | 0.05 | — | — | — | | |
| Sodium chloride | 0.65 | 0.9 | — | 0.7 | | |
| Potassium chloride | 0.15 | — | 1.15 | 0.2 | | |
| EDTA•2Na | 0.05 | — | — | — | | |
| Nonionic surfactants | — | — | — | — | | |
| PHMB | 0.0001 | — | — | — | | |
| PQ-6 (M.W. 8500) | — | — | — | — | | |
| PQ-6 (M.W. 150000) | — | 0.0001 | 0.0001 | 0.0001 | | |
| PQ-6 (M.W. 240000) | — | — | — | — | | |
| PQ-6 (M.W. 500000) | — | — | — | — | | |
| PQ-6 (M.W. 1200000) | — | — | — | — | | |
| PQ-7 (M.W. 10000) | 0.001 | — | — | — | | |
| PQ-7 (M.W. 180000) | — | — | — | — | | |
| pH | 7.6 | 6.5 | 6.4 | 6.4 | | |
| Osmotic pressure (mOms) | 274 | 286 | 272 | 274 | | |
| Osmotic pressure rate (osmatic pressure 286) | 0.96 | 1.00 | 0.95 | 0.96 | 0.00 | 0.00 |
| Acanthamoeba castellanii | 0.78 | 0.50 | 0.50 | 0.50 | 0.05 | 0.30 |
| Pseudomonas aeruginosa | >5.25 | 0.90 | 0.91 | 1.17 | 3.57 | 4.51 |

TABLE 3

| | Examples | | | | | | | | | | Comparative Examples | | | | | | | | | | | |
|---|---|---|---|---|---|---|---|---|---|---|---|---|---|---|---|---|---|---|---|---|---|---|
| Safety | 6 | 7 | 8 | 9 | 10 | 13 | 14 | 15 | 16 | 18 | 5 | 6 | 7 | 8 | 9 | 10 | 11 | 12 | 13 | 15 | MPS(1) | MPS(2) |
| 20% | Δ | Δ | Δ | Δ | Δ | Δ | Δ | Δ | Δ | Δ | Δ | Δ | x | Δ | Δ | Δ | Δ | Δ | Δ | Δ | Δ | x |
| 10% | ○ | ○ | ○ | ○ | ○ | ○ | ○ | ○ | ○ | ○ | ○ | ○ | ○ | Δ | ○ | ○ | ○ | ○ | ○ | ○ | ○ | x |
| 5% | ○ | ○ | ○ | ○ | ○ | ○ | ○ | ○ | ○ | ○ | ○ | ○ | ○ | ○ | ○ | ○ | ○ | ○ | ○ | ○ | ○ | Δ |
| 2.5% | ○ | ○ | ○ | ○ | ○ | ○ | ○ | ○ | ○ | ○ | ○ | ○ | ○ | ○ | ○ | ○ | ○ | ○ | ○ | ○ | ○ | ○ |

"PQ" in Tables 1 and 2 represents polyquaternium and specifically represents the following materials:
PQ-6 (MW 8500): PAS-H-1L (NITTOBO MEDICAL)
PQ-6 (MW 150,000): MERQUAT 100 (Lubrizol)
PQ-6 (MW 240,000): ME Polymer H-40W (TORO Chemical Industry)
PQ-6 (MW 500,000): UNISENCE FPA1002L (SENKA Corporation)
PQ-6 (MW 1,200,000): UNISENCE FPA700E (SENKA Corporation)
PQ-7 (MW 10,000): PAS-J-81-L (NITTOBO MEDICAL)
PQ-7 (MW 180,000): PAS-J-81 (NITTOBO MEDICAL)

[Test Results]

As indicated by Tables 1 and 2, for at least one cationic polymer selected form the group consisting of different types of polyquaterniums 6 and polyquaterniums 7, those having a molecular weight of 150,000 to 1,200,000 have proven to show disinfection effects against *Acanthamoeba* and provide contact lenses with excellent shape stability. As indicated by Table 3, for at least one cationic polymer selected form the group consisting of different types of polyquaterniums 6 and polyquaterniums 7, those having a molecular weight of 150,000 to 240,000 have proven to be highly safe on eye tissue. In this regard, since high-molecular-weight compounds are generally considered safer than low-molecular-weight compounds, and since low-molecular-weight compounds tend to be incorporated into contact lenses and may be released on eyes while the contact lenses are worn on eyes, it is suggested that polyquaterniums 6 and polyquaterniums 7 with molecular weights in the range of 150,000 to 240,000 are highly safe on eye tissue. In addition, it was confirmed that the test samples prepared so that their osmotic pressures were around 220 exhibit anti-*Acanthamoeba* effects (i.e., the logarithmic difference according to the evaluation method 2 is 1.0 or higher). It is suggested that the anti-*Acanthamoeba* effects are observed by even adjusting the osmotic pressure to around 375 since the disinfection effects to *Acanthamoeba* tend to increase as the osmotic pressure increases.

Accordingly, the anti-*Acanthamoeba* contact lens solution in one aspect of the present invention provides a contact lens solution that exhibits excellent disinfection effects against *Acanthamoeba* while ensuring safety comparable to or even higher than commercially available products and having versatility that makes the solution applicable to a wide range of contact lenses.

INDUSTRIAL APPLICABILITY

Being highly safe on eye tissue, applicable to a wide range of contact lenses and having excellent disinfection effects against *Acanthamoeba*, the anti-*Acanthamoeba* contact lens solution in one aspect of the present invention can be used as a contact lens care solution such as MPS to reduce or avoid the risk of the wearer affected with keratitis caused by *Acanthamoeba*, thus contributing to the health and welfare of the wearer of the contact lens.

The invention claimed is:

1. An anti-*acanthamoeba* contact lens solution comprising a cationic polymer having an average molecular weight in a range of 150,000 to 1,600,000 and having in its molecule a diallyldimethylammonium chloride unit represented by general formula (I):

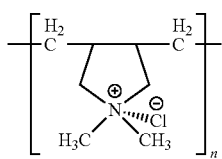

wherein n is an integer determined such that the average molecular weight of the polymer is in the range specified above;
a borate buffer;
a chelating agent; and
an inorganic salt;
wherein the cationic polymer is at least a cationic polymer selected from the group consisting of a cationic polymer wherein the polymer unit in its molecule is the diallyldimethylammonium chloride unit, a cationic polymer wherein the polymer units in its molecule are the diallyldimethylammonium chloride unit and an acrylamide unit, a cationic polymer wherein the polymer units in its molecule are the diallyldimethylammonium chloride unit and an acrylic acid unit, and a cationic polymer wherein the polymer units in its molecule are the diallyldimethylammonium chloride unit, an acrylamide unit and an acrylic acid unit;
wherein the anti-*acanthamoeba* contact lens solution comprises no biguanide-based disinfectant and no quaternary ammonium-based disinfectant;
wherein the chelating agent is ethylenediaminetetraacetic acid;
wherein the inorganic salt is an inorganic salt selected from the group consisting of sodium chloride and potassium chloride or a combination thereof; and
wherein the cationic polymer is present in an amount of from 0.0001 to 0.01 w/v %, the borate buffer is present in an amount of from 0.05 to 1.0 w/v %, the chelating agent is present in an amount of from 0.01 to 0.05 w/v %, and the inorganic salt or the combination thereof is present in a total amount of from 0.75 to 1.0 w/v %.

2. The anti-*acanthamoeba* contact lens solution according to claim 1, wherein the cationic polymer is a cationic polymer having an average molecular weight in a range of 150,000 to 1,200,000.

3. The anti-*acanthamoeba* contact lens solution according to claim 1, wherein the cationic polymer is a cationic polymer having an average molecular weight in a range of 200,000 to 500,000.

4. The anti-*acanthamoeba* contact lens solution according to claim 1, wherein the cationic polymer is polyquaternium-6 or polyquaternium-7.

5. A method of reducing the risk of *acanthamoeba* infection in a contact lens wearer, comprising:
contacting a contact lens and/or an eye of the wearer with the solution of claim 1.

6. The method of claim 5, wherein said wearer has keratitis.

7. The method of claim 5, wherein the method further comprises storing said contact lens in said solution.

8. The method of claim 5 wherein the method further comprises directly applying said solution to the eye of the wearer.

9. The method of claim 5, wherein the method further comprises washing said contact lens with said solution.

10. The anti-*acanthamoeba* contact lens solution according to claim 1, wherein the amount of the borate buffer is 0.2 w/v %.

11. The anti-*acanthamoeba* contact lens solution according to claim 1, wherein the amount of chelating agent is 0.05 w/v %.

* * * * *